United States Patent [19]
Matsui et al.

[11] Patent Number: 5,918,986
[45] Date of Patent: Jul. 6, 1999

[54] BEARING FOR HIGH-SPEED ROTATING EQUIPMENT

[75] Inventors: Akira Matsui, 28-44, Tenjugaoka-cho, Hanazono, Ukyo-ku, Kyoto, 616; Yoshinori Morita, Shiga; Masahiro Kato; Masaharu Hori, both of Mie, all of Japan

[73] Assignees: Akira Matsui; J. Morita Manufacturing Corporation, both of Kyoto; NTN Corporation, Osaka, all of Japan

[21] Appl. No.: 08/939,646

[22] Filed: Sep. 30, 1997

[30] Foreign Application Priority Data

Oct. 1, 1996 [JP] Japan .................................. 8-278547

[51] Int. Cl.⁶ .......................... F16C 33/56; F16C 33/66
[52] U.S. Cl. ...................... 384/470; 384/527; 384/902
[58] Field of Search ............................ 384/462, 463, 384/468, 470, 523, 527, 902; 433/132; 508/100, 101

[56] References Cited

U.S. PATENT DOCUMENTS

| | | | |
|---|---|---|---|
| 3,027,626 | 4/1962 | Murphy | 384/527 X |
| 3,376,084 | 4/1968 | McKee | 433/132 |
| 3,886,660 | 6/1975 | Thornton, Jr. et al. | 433/101 X |
| 4,541,739 | 9/1985 | Allen et al. | 384/470 |
| 5,346,724 | 9/1994 | Ohgake et al. | 427/384 |
| 5,401,105 | 3/1995 | Suzuki et al. | 384/527 X |
| 5,529,401 | 6/1996 | Gabelli et al. | 384/527 X |
| 5,538,654 | 7/1996 | Lawate et al. | 508/308 |
| 5,562,446 | 10/1996 | Morita | 433/132 |
| 5,707,718 | 1/1998 | Matsukawa et al. | 384/902 X |
| 5,736,493 | 4/1998 | Garmier | 508/491 |

FOREIGN PATENT DOCUMENTS

| | | |
|---|---|---|
| 5-43884 | 7/1993 | Japan . |
| 6-165790 | 6/1994 | Japan . |
| 6-212179 | 8/1994 | Japan . |
| 7-10553 | 2/1995 | Japan . |

*Primary Examiner*—Thomas R. Hannon
*Attorney, Agent, or Firm*—Koda & Androlia

[57] ABSTRACT

A rolling bearing for a high-speed rotating equipment is constructed of an outer ring, an inner ring, rolling elements and a retainer to rotatably support at least a rotary shaft thereon. The retainer is composed of a molded porous synthetic resin body having a porous portion of a communicated structure in at least a part thereof. Further, the is lubricated with a lubricating oil comprising a nondrying vegetable oil.

8 Claims, 2 Drawing Sheets

BEARING FOR HIGH-SPEED ROTATING EQUIPMENT

BACKGROUND OF THE INVENTION a) Field of the Invention

This invention relates to a rolling bearing for a high-speed rotating equipment employed in a field where high speed and high safety are required, such as a medical, food-processing or aerospace equipment.

More specifically, the present invention is concerned with a rolling bearing as a principal element of a high-speed rotating equipment such as a dental high-speed rotating cutter (dental air turbine hand piece), which assures stable high-speed rotation, has high biosafety, and is equipped with durability sufficient to withstand sterilization treatment (autoclaving) under high temperature and high pressure.

b) Description of the Related Art

A high-speed rotating equipment, especially a high-speed cutter for rotating a cutting tool at high speeds is generally constructed of a rotary shaft for fixedly holding various cutting tools thereon, a drive unit for rotating the rotary shaft, and a bearing unit rotatably supporting the rotary shaft.

As a high-speed cutter of this type, an odontotherapeutic high-speed cutter (i.e., air turbine hand piece) can be mentioned by way of example.

Bearing units for the above-mentioned odontotherapeutic high-speed cutters (i.e., air turbine hand pieces) are known to include those having a ball bearing system making use of balls (rolling elements) and those equipped with a (non-contact) air bearing system making use of an air bearing.

Paying attention, for example, to the bearing mechanisms of dental air turbine hand pieces, two types of air turbine hand pieces are known, one being of the ball bearing turbine type and the other of the air bearing turbine type.

The former type, i.e., the ball bearing turbine type can be considered to be a high-speed rotation type for approximately 200,000 to 400,000 rpm, while the latter type, that is, the air bearing turbine type can be considered to be a super high-speed rotation type for approximately 300,000 to 500,000 rpm.

It is however to be noted that the above-described revolution speeds of the ball bearing turbine type and the air bearing turbine type are general values. For example, the dental air turbine hand piece already proposed by the present inventors (U.S. Pat. No. 5,562,446) is of the ball bearing turbine type. Nonetheless, it has high performance so that super high-speed rotation can be achieved.

To facilitate the understanding of the conventional art and this invention, a description will now be made about the construction of an equipment to which a bearing according to the present invention, said bearing comprising a lubricating oil and a porous retainer, is applied, namely, of a dental high-speed cutter (i.e., a dental air turbine hand piece).

FIG. 1 to FIG. 2 show the construction of the dental air turbine hand piece, in which FIG. 1 is a perspective view illustrating the overall construction and FIG. 2 is a cross-sectional view illustrating the internal construction of a head portion and a neck portion in particular.

As is depicted in FIG. 1, the dental air turbine hand piece designated generally by letter A is composed of a head portion H, which carries a cutting tool B(5) fixedly held on a rotor shaft (drive shaft) of an air turbine, and a grip portion G.

A neck portion N of the grip portion G is connected to the head H, and is internally provided with means for supplying compressed air to the air turbine arranged within the head portion H and also for discharging compressed air from the air turbine.

FIG. 2 illustrates the internal construction of the head portion H and the neck portion N of the dental air turbine hand piece A.

As is illustrated in the figure, in the head portion H, a turbine rotor shaft 3 with turbine blades 2 disposed at a peripheral edge portion thereof is arranged within a chamber 11 of a head 1, and the turbine rotor shaft 3 is rotatably supported within the head 1 by way of a bearing unit 4.

The head 1 is composed of a head main part 12 and a cap part 13. Within the head main part 12, the bearing unit 4 is arranged to rotatably support the turbine rotor shaft 3. To perform treatment, the cutting tool 5 is fixedly held in a bore which is formed through the turbine rotor shaft 3 along a central axis thereof. Incidentally, the cutting tool 5 is provided on a peripheral side wall thereof with a chuck 51 for holding the cutting tool 5 in place within the bore.

The bearing unit 4 is of the ball bearing type and is constructed of an inner ring 41, an outer ring 42, rolling elements 43 and a retainer 44. The bearing unit 4 may be provided on an outer periphery or side wall thereof with O-rings for providing the bearing unit with self-centering function and/or with known wave washers for enhancing the rigidity of the shaft.

A main part 6 of the neck portion N is provided with an air supply passage 7 and an air inlet 71 for supplying compressed air to the turbine blades 2 arranged within the chamber 11 and also with air discharge passages 8,9 and air outlets 81,91 for discharging compressed air from the chamber 11.

In the above-described internal construction of the dental air turbine hand piece A as illustrated in FIG. 2, the means for supplying and discharging compressed air is the one already proposed by the present inventors (U.S. Pat. No. 5,562,446) and is of a new construction totally unseen in the conventional art.

Accordingly, FIG. 2 contains other reference symbols in addition to those referred to in the above to describe the individual elements (members). Although a description of these additional symbols is omitted herein, the construction of the conventional dental air turbine hand piece can be easily understood on the basis of FIG. 2.

The dental air turbine hand piece A—which is equipped with the air supply and discharge means shown in FIG. 2 and already proposed by the present inventors—belongs to the category of conventional hand pieces with a rolling bearing built therein, but makes it possible to obtain rotation of an extremely high speed and hence a large torque.

In the above-described dental air turbine hand piece of the ball bearing type, its bearing unit is in the form of a miniature bearing unit. Since the turbine rotor shaft rotates at a high speed of approximately 200,000 to 400,000 revolutions per minute, the temperature inside the bearing unit becomes high and further, the bearing unit is exposed to a large stress. For a lubricating oil to be applied to a bearing which is used under the above-described severe conditions, it is therefore extremely important to control its quality and properties.

Further, the above-described dental air turbine hand piece of the ball bearing type is used in the oral cavity. Accordingly, the dental air turbine hand piece is used by spraying or dropping a lubricating oil to the bearing unit, in other words, is used under an environment of minimum lubrication, and is subjected to high-pressure and high-temperature treatment for sterilization and disinfection (which is also called "autoclaving", which is applied under the following conditions: steam pressure, 2.4 kg/cm$^2$; temperature, 135° C.; time, 5 minutes).

As a rolling bearing for use in the above-described dental air turbine hand piece, one capable of meeting conditions similar to those mentioned above is therefore required. In particular, as a retainer which acts as an important element in a lubrication system, one capable of satisfying conditions similar to those mentioned above is required.

Further, the lubricating oil for use in the above bearing is also required to have properties sufficient to withstand such severe use conditions, such as oxidation resistance.

Conventional examples of the above-described retainer for rolling elements (balls) include those made of polyimide resins or fiber-layer-containing phenol resins from the viewpoint of the above-described property requirements. These conventional retainers are however not considered to be sufficient.

As lubricating oils applied to rolling bearings in high-speed rotating equipments, on the other hand, a variety of lubricating oils have been used or proposed.

For example, it is widely practiced to supply a lubricating oil by spraying it with flon or LPG. As lubricating oils, those making use of refined mineral oils, such as paraffin, as base oils are known.

The above-described lubricating oils are typically of the petroleum base and are prepared by fractionating and refining petroleum into various fractions and incorporating additives, such as an oxidation inhibitor, therein as needed.

As base oil components of the above-described lubricating oils, there are known synthetic oils such as glycol esters and low molecular weight polyolefins in addition to natural mineral oils. Furthermore, edible oils such as animal oils and vegetable oils are also known to be in use as lubrication oils for precision machines, machine tools, ship engines and the like. In general, however, these edible oils are used by being added in proportions of from 10 to 20 wt. % to lubricating oil of the mineral oil base.

Incidentally, these edible oils have a problem in oxidation resistance. It is therefore the common practice to use such edible oils in combination with one or more of various oxidation inhibitors.

In view of the above-described severe use conditions for dental air turbine hand pieces, dental air turbine hand pieces equipped with retainers impregnated with fluorinated oils, which have excellent heat resistance, permit sterilization and disinfection (autoclaving) and have superb lubricity, have been proposed recently in Japanese Patent Publication (Kokoku) No. HEI 5-43884 and Japanese Utility Model Application Laid-Open (Kokai) No. HEI 7-10553.

Incidentally, the retainers are in the form of porous members obtained by sintering powder of a polyimide resin.

The fluorinated oils have properties such that they are inactive, are excellent in heat resistance, chemical resistance and solvent resistance and, even when exposed to high temperatures, do not form a solid deterioration material. It is therefore possible to consider that the above-described proposed dental air turbine hand pieces have used these properties for the retainers.

Further, Japanese Patent Application Laid-Open (Kokai) No. HEI 6-165790 discloses an embodiment of impregnating with a lubricating oil a snap retainer of a ball bearing in a dental air turbine hand piece to be described briefly hereinafter, although its direct subject matter is the snap retainer itself.

Specifically, in the dental air turbine hand piece disclosed in Japanese Patent Application Laid-Open (Kokai) No. HEI 6-165790 referred to in the above, the retainer of the ball bearing is characterized in that:

(i) the retainer is a snap retainer, in which a ball-holding pocket is formed on one side of a synthetic resin cylinder having a fabric-made fiber layer therein, and chamfered portions are formed on opening-side end edges of the pocket; and (ii) the fiber layer of the retainer is impregnated with a lubricating oil.

Incidentally, the snap retainer of the ball bearing disclosed in Japanese Patent Application Laid-Open (Kokai) No. HEI 6-165790 is to improve the balance of rotation by the feature (i), thereby making it possible to protect the retainer from wearing and also to avoid an increase in rotating torque, both of which would otherwise occur due to contact between the retainer and the outer ring.

However, the specific composition of the lubricating oil impregnated in the retainer is not clear in Japanese Patent Application Laid-Open (Kokai) No. HEI 6-165790. As a matter of fact, Japanese Patent Application Laid-Open (Kokai) No. HEI 6-165790 does not disclose whatsoever the specific composition of the edible oil, although it describes an embodiment of charging an edible oil into a housing in the description of the conventional art. It is the present inventors' belief that the lubricating oil or edible oil disclosed in Japanese Patent Application Laid-Open (Kokai) No. HEI 6-165790 is still no better than the level of the conventionally-proposed lubrication oils in view of the technical level in the present field of art.

Further, Japanese Patent Application Laid-Open (Kokai) No. HEI 6-212179 discloses mixing of ceramic powder in a lubricating oil to reduce the replenishing frequency of a lubricating oil to a bearing of a dental air turbine. This is a proposal based on a finding that advance mixing of ceramic powder in a lubricating oil can improve the life time of the lubricating oil.

The above-described various lubricating oils, which have been proposed to date, are still accompanied by various drawbacks which should be improved in order to permit their application in high-speed rotating equipments such as odontotherapeutic air turbine hand pieces having rolling bearings.

For example, the above-described lubricating oils of the mineral oil base, such as of the liquid paraffin base, or of the synthetic oil base or the lubricating oils obtained by adding edible oils to them still involve matters to be improved from the viewpoint of biosafety and environmental conservation.

In addition, the fluorinated oils proposed in the above-described Japanese Patent Publication (Kokoku) No. HEI 5-43884 and Japanese Utility Model Application Laid-Open (Kokai) No. HEI 7-10553, such as perfluoropolyether (PFPE) and perfluoropolyalkyl ether (PFAE), are excellent in heat resistance, chemical resistance and solvent resistance and, even when exposed to high temperatures, form no solid deterioration material. They are accordingly preferred as lubricating oils for high-speed rotating equipments. They however still involve matters to be improved from the viewpoint of environmental destruction and biosafety.

Furthermore, the above-described Japanese Patent Application Laid-Open (Kokai) No. HEI 6-165790 discloses impregnation of a retainer of a rolling bearing, which is formed of a shaped member made of a phenol resin and having a fiber layer, with a lubricating oil, and suggests use of an edible oil as the above-described lubricating oil. As will be descried in detail subsequently herein, a great majority of general edible oils are drying oils and, when they become dry, they are formed into resinous solids. They are accordingly not suited as durable lubricating oils for bearings.

As has been described above, most of general edible oils are dry oils and are susceptible to oxidation. It is therefore the common practice to use them by adding a synthetic oxidation inhibitor therein. In an edible-oil-base lubricating oil composed primarily of the above-described drying oil and added with an oxidation inhibitor, it is necessary to keep in mind the potential risk that a reaction product to be formed between the oxidation inhibitor and a metal dissolved out from a bearing system may be a material harmful for the body.

According to the above-described Japanese Patent Application Laid-Open (Kokai) No. HEI 6-212179, ceramic powder is mixed in a lubricating oil to improve the life time of the lubricating oil so that the replenishing frequency of the lubricating oil to a lubrication system can be reduced. In an odontotherapeutic cutter of the high-speed rotation type (air turbine hand piece), however, the race (retainer) and balls of the bearing are ground by the ceramic powder so that a metal harmful for the body may be dissolved out, or a serious damage may be given to the bearing mechanism when the lubricating oil becomes scarce under the environment of minimum lubrication.

As has been described above, the conventional lubricating oils for rolling bearings, said oils being for use in high-speed rotating equipments, for example, odontotherapeutic high-sped cutters (air turbine hand pieces), are still accompanied by drawbacks when evaluated in view of the following properties:

(i) biosafety (reduced harm to the body), (ii) environmental conservation (safety), (iii) heat resistance (the possibility of sterilization and disinfection by autoclaving), and (iv) durable lubrication system.

SUMMARY OF THE INVENTION

The present invention has been completed in view of the above-described problems of the bearings in the conventional high-speed rotating equipments.

Incidentally, the direct motive for the present invention resided in the lack of a lubricating oil of excellent properties for the high-performance and high-speed rotating, dental air turbine hand piece of the ball bearing turbine type previously proposed by the present inventors (U.S. Pat. No. 5,562,446).

The present invention has been completed on the basis of a finding that in a rolling bearing for a high-speed rotating equipment, especially in a retainer for rolling elements (balls), said retainer being an important element in the bearing, a lubrication system of excellent characteristics not found in the conventional art can be achieved when the retainer is composed of a molded body of a particular porous resin and the retainer is impregnated with a specific lubricating oil, specifically a nondrying vegetable oil.

The present invention provides a rolling bearing having high performance such that it has sufficient durability under high-speed rotation in a high-speed cutting equipment such as a dental air turbine hand piece, it possesses heat resistant sufficient to withstand high temperature and high pressure such as autoclaving sterilization, and is excellent in biosafety.

In other words, the present invention provides a rolling bearing as a principal element in a high-speed rotating equipment of the ball bearing type operated at 200,000 rpm or higher or even at 300,000 rpm or higher such as an odontotherapeutic high-speed cutter, said lubricating oil being capable of establishing a durable lubrication system without needing a reduction in revolution speed in the high-speed rotating equipment; and a rolling bearing lubricated with the lubricating oil.

Describing the present invention in brief, the present invention relates a rolling bearing for a high-speed rotating equipment constructed at least of an outer ring, an inner ring, rolling elements and a retainer, characterized in that the retainer:

(i) is composed of a molded porous resin body having a porous portion of a communicated structure (communicated porous portion) in least a part thereof, and (ii) has been obtained by impregnating the porous portion of the communicated structure with a lubricating oil comprising a nondrying vegetable oil.

Evaluating on the basis of the lubricating oil composed primarily of the nondrying vegetable oil and applied to the rolling bearing according to the present invention for a high-speed rotating equipment such as an odontotherapeutic high-speed cutter (air turbine hand piece), the rolling bearing exhibits excellent advantages as will be described next.

(i) The lubricating oil according to the present invention, which comprises the nondrying vegetable oil, is excellent in various properties, i.e., in biosafety, environmental conservation, heat resistance (autoclaving resistance) and bearing durability.

Further, it is also excellent in economy because its cost is lower than those of conventionally-proposed lubricating oils of the fluorinated oil base.

(ii) Vegetable oils other than nondrying vegetable oils, such as semidrying oils and drying oils and paraffin oil (liquid paraffin), are observed to undergo considerable color changes when tested, namely, left over at 135° C. for 175 hours in air. In other words, these oils of various varieties are inferior in oxidation resistance.

In contrast, nondrying vegetable oils useful in the present invention, such as olive oil and arachis oil, do not show color changes in the above-described test, and are excellent in oxidation resistance.

(iii) The lubricating oil according to the present invention, which is composed primarily of a nondrying vegetable oil and is applicable to a rolling bearing in a high-speed rotating equipment such as a dental air turbine hand piece, has a high biodegradation speed and, even when evaluated based on the Interim Water Quality Standards for Effluents (an ordinance of the Office of the Prime Minister), is more preferable than conventional mineral oils. Incidentally, according to the above-mentioned Interim Water Quality Standards for Effluents, the permissible limit for effluents is 30 mg/liter in the case of vegetable oils as opposed to 5 mg/liter in the case of conventional mineral oils.

DETAILED DESCRIPTION OF THE INVENTION AND PREFERRED EMBODIMENTS

The technical constitution and embodiments of the present invention will hereinafter be described in detail.

In the rolling bearing according to the present invention for the high-speed rotating equipment, the first feature resides in that the retainer for the rolling elements (balls), said retainer being a principal element of the rolling bearing, is composed of the molded porous body of the specific matrix material.

In the rolling bearing according to the present invention for the high-speed rotating equipment, the second feature resides in that the retainer has been obtained by impregnating the molded porous body of the specific matrix material with the specific lubricating oil, more specifically the lubricating oil comprising the nondrying vegetable oil.

The technical constitution of the present invention will hereinafter be described in the order of the above-described first and second features of the present invention.

A description will first be made of the constitution of the retainer as the first feature of the present invention.

The first embodiment of the retainer according to the present invention will be described next.

The first embodiment of the retainer according to the present invention is composed of a molded body of a porous polyimide resin.

Figure 3:
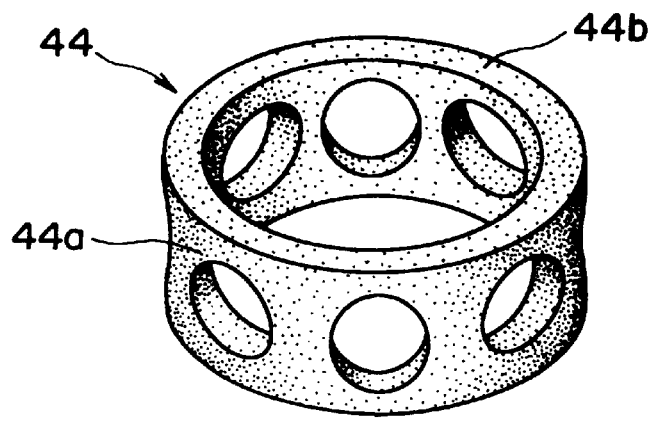
FIG. 3 is a perspective view of a retainer shown in FIG. 2.

FIG. 3 is a perspective view of a retainer 44 composed of the above-mentioned molded body of the porous polyimide resin. In the figure, symbol 44a indicates a retainer main part, and symbol 44b designates pores.

Figure 1:
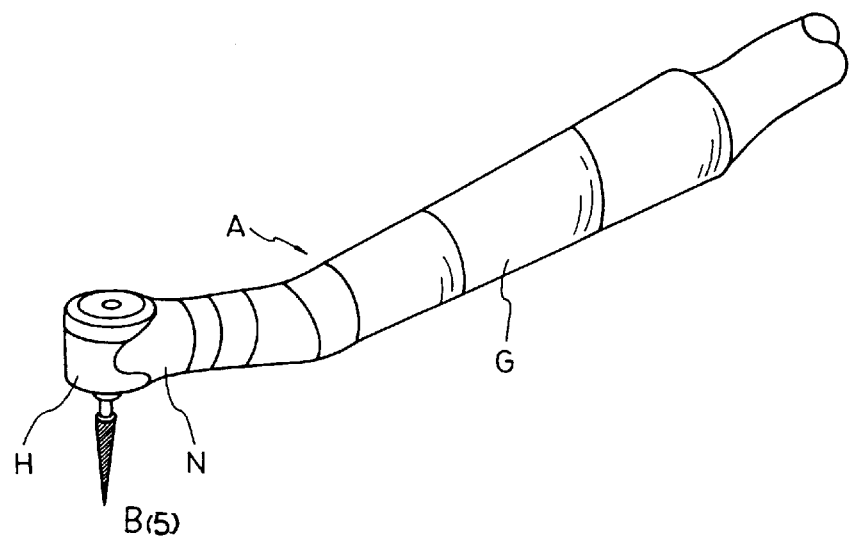
FIG. 1 is a perspective view of a dental air turbine hand piece equipped with a rolling bearing according to a first embodiment of the present invention.

Incidentally, the retainer 44 is applied to the dental air turbine hand piece of the ball bearing type described with reference to FIG. 1 to FIG. 2.

In the retainer which is composed of the molded porous polyimide resin body according to the present invention, the above-mentioned polyimide resin (hereinafter abbreviated as "the PI resin") is a resin obtained by subjecting an aromatic carboxylic acid and an aromatic amine to condensation polymerization and containing imide bonds in the backbone thereof (which may be either thermoplastic or thermosetting), and is excellent in heat resistance, chemical resistance, mechanical properties and electrical characteristics.

In the present invention, the term "PI resin" should be interpreted to also include polyamideimide resins (hereinafter abbreviated as "the PAI resins") containing imide bonds and amide bonds in their backbones.

In the present invention, a commercially-available PI resin or PAI resin can be conveniently used as the PI resin or PAI resin for molding the retainer. As commercially-available PI resins and PAI resins, the following resins can be exemplified including their chemical structural formulas.

(i) PI resins:
(1) "P94-HT" [trade name; product of Lenzing AG, Austria; represented by the below-described chemical formula (1) in which R represents an alkylene group];
(2) "TI-3000" [trade name; product of Toray Industries, Inc.; represented by the below-described chemical formula (2)];
(3) "UIP-S" [trade name; product of Ube Industries, Ltd.; represented by the below-described chemical formula (3)];
(4) "Vespel" [trade name; product of E. I. du Pont de Nemours & Co., Ltd.; represented by the below-described chemical formula (2)];
(5) "Aurum" [trade name; product of Mitsui-Toatsu Chemicals Inc.; represented by the below-described chemical formula (4)]; and
(6) Others, including "Meldin 8100" and "Meldin 900", products of Furon, U.S.A.

(ii) PAI resins:
(1) "Torlon 4000 TF" [trade name; product of Amoco Chemical Corp.; represented by the below-described chemical formula (5) in which Ph represents a phenylene group].

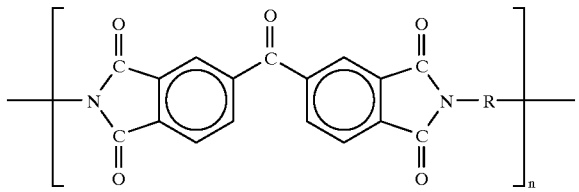

Chemical formula (1)

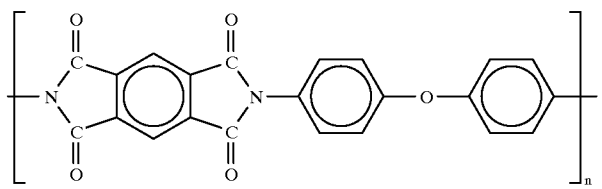

Chemical formula (2)

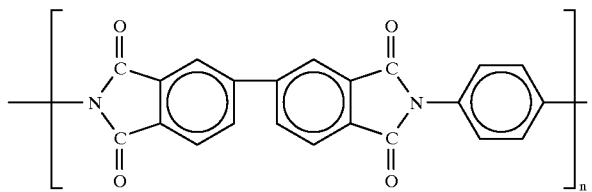

Chemical formula (3)

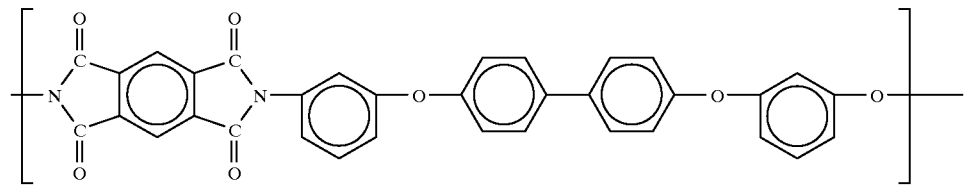

Chemical formula (4)

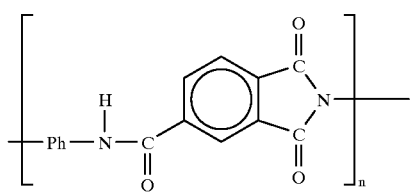

Chemical formula (5)

The retainer composed of the above-described molded porous PAI resin body can be produced by compressing and sintering PAI resin powder the average particle size of which has been classified and sifted to 15 to 50 µm.

By adjusting the average particle size, pressure and the like of the resin powder as desired in the above-described sinter molding, the retainer is produced in a porous structure containing 5 to 20% by volume of communicating pores. As will be described in detail subsequently herein, the communicating pores are next impregnated with a specific lubricating oil (base oil: nondrying vegetable oil) to produce the retainer according to the present invention.

If powder of fine particle sizes smaller than 15 µm is mixed in the resin powder as the raw material, the pores, namely, the spaces are filled with such fine powder in the retainer composed of the molded porous PAI resin body. This leads to variations in the porosity values of products. The above-described classification and sifting are therefore needed.

If powder of large particles sizes greater than 50 µm is mixed conversely, large spaces are formed between particles so that the percent retention (percent oil retention) of the impregnated oil during high-speed rotation is lowered and further, the strength of the retainer is reduced. Mixing of powder of such a large particle size is therefore not preferred.

Figure 4:
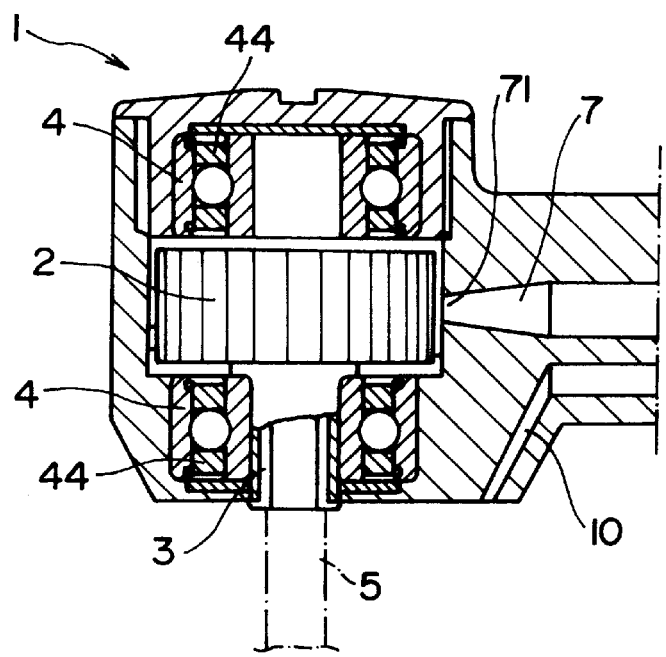
FIG. 4 is a cross-sectional view similar to FIG. 2, but illustrates a dental air turbine hand piece equipped with a rolling bearing according to a second embodiment of the present invention.
Figure 5:
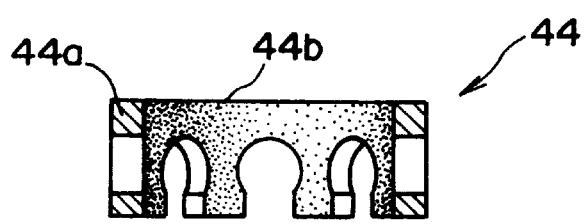
FIG. 5 is a cross-sectional view of a retainer depicted in FIG. 4.

FIG. 4 to FIG. 5 illustrate another embodiment of the retainer 44 composed of the molded porous PAI resin body.

Figure 2:
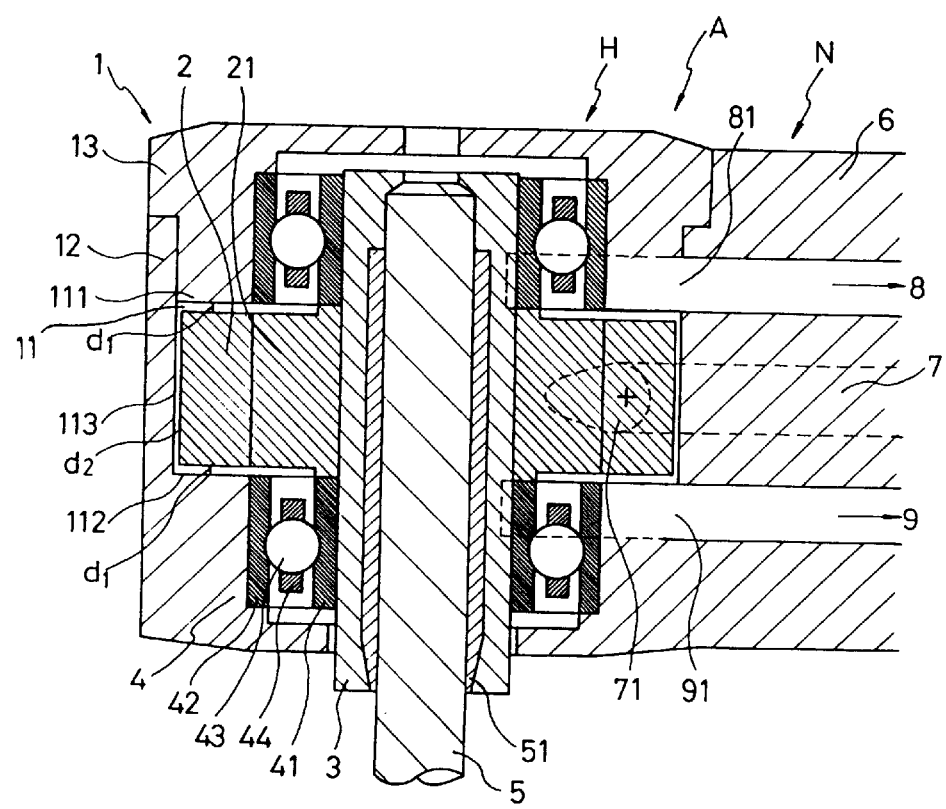
FIG. 2 is a cross-sectional view of a head portion and a neck portion of the dental air turbine hand piece of FIG. 1.

Specifically, FIG. 4 illustrates a dental air turbine hand piece of a structure different from the above-described hand piece shown as an application example of a retainer 44 in FIG. 2. A description of the structure of the dental air turbine hand piece in FIG. 4 is omitted herein, because it is clear from the above-described corresponding FIG. 2. Although not shown in the drawing, the bearing may be provided with a seal.

On the other hand, FIG. 5 illustrates the shape and structure of the retainer 44 and corresponds to the above-described FIG. 3. In FIG. 5, symbol 44a indicates a main retainer part while symbol 44b designates pores.

The second embodiment of the retainer according to the present invention will be described next.

The second embodiment of the retainer according to the present invention is composed of a molded porous PI resin body.

The retainer composed of the molded porous PI resin body can be produced in a similar manner as the above-described sinter molding of the powder of the PAI resin. Namely, a molded porous PI resin body containing communication pores in a proportion as much as 5 to 20% by volume can be produced by compressing and sintering PI resin powder the average particle size of which has been classified and sifted to 15 to 50 µm.

In the above-described first and second embodiments, the retainers were formed by sintering. The forming process is however not limited to them. For example, a retainer may be molded by a process which is to be described hereinafter.

A PI resin, which serves to make up a porous matrix material, is blended with another heat-resistant resin. This another heat-resistant resin has a molding temperature range close to the PI resin and, when treated with a solvent in the presence with the PI resin, is solely dissolved out. The blend is then molten and molded into a retainer of a desired shape. From the thus-molded retainer, only the another heat-resistant resin is dissolved out with the solvent, whereby a porous retainer can be obtained.

In the above-described molding process of the retainer, the term "PI resin" embraces PAI resins.

Incidentally, usable examples of the another heat-resistant resin can include polyether sulfone (PES), polyether imide (PEI), polyarylate (PAR) and polysulfone (PSF). Further, usable examples of the solvent can include methylene chloride (dichloromethane), chloroform, methyl ethyl ketone, tetrahydrofuran, N-methylpyrrolidone and N,N-dimethylformamide.

Compared with the above-described retainer made of the porous PAI resin, the above-described retainer made of the porous PI resin has merits such that, when the retainer runs out of the lubricating oil, the retainer does not melt and the bearing does not become no longer usable and that the PI resin is slow in moisture-absorbing speed and hence permits easy control of raw material powder and molded bodies. For the reasons mentioned above, the latter resin, i.e., the PAI resin is classified as a fusible resin.

In sterilization treatment (autoclaving), on the other hand, prevention from infection, especially to HIV is also required in recent years. It is therefore required to perform the treatment under severer conditions (for example, 2.4 kg/cm$^2$, 135° C., 5 minutes) than the conventional treatment conditions. In spite of such severe conditions, the above-described retainer made of the porous PI resin can withstand temperatures up to about 200° C.

A third embodiment of the retainer according to the present invention will be described next.

The third embodiment of the retainer according to the present invention is composed of a shaped phenol resin body having a fiber layer which can be considered to be a communicated pore layer. A shaped phenol resin body provided with a fiber layer of this type can be impregnated with a lubricating oil by making use of the fiber layer.

In the present invention, the shaped phenol resin body with the resin layer incorporated therein (which may hereinafter be called the "porous PR") has function to be impregnated with a lubricating oil through the fiber layer (fabric) although this function is different from the impregnable function of the above-described molded porous PI or PAI resin body (which may hereinafter be called the "porous PI/PAI.R") that the lubricating oil is impregnated through the communication pores. The above-described shaped phenol resin body with the fiber layer (fabric) incorporated therein is therefore taken as a molded resin body having a porous portion (communication pores) in the present invention, although the term may not be fully accurate.

The phenol resin retainer provided with a fiber layer of the above-mentioned type can be produced, for example, by the process disclosed in Japanese Patent Application Laid-Open (Kokai) No. HEI 6-165790.

For example, the above-described shaped phenol resin body with the fabric incorporated therein can be produced by:

(i) a process in which the fabric is rolled plural times into a pipe-like shape, the rolled fabric is impregnated with a phenol resin while maintaining it in a vacuum state, and the phenol resin is then hardened to form a porous cylindrical body, or (ii) a process in which the fabric impregnated with a phenol resin is rolled plural times, and the rolled fabric is then heated under pressure into a porous cylindrical body.

The porosity of the above-described shaped phenol resin body with the fabric incorporated therein can be similar to that of the above-described PI resin, and a porous one having a porosity of from 5 to 20% by volume can be used.

A detailed description will next be made about the composition of the lubricating oil as the second feature of the present invention, namely, about the specific lubricating oil impregnated in the molded porous body which makes up a main part of the above-described retainer.

The second feature of the present invention resides in that, in a high-speed rotating equipment [for example, a high-speed cutter (air turbine hand piece)] having a rolling bearing element composed of an outer ring, an inner ring, rolling elements (ball bearings) and a porous retainer made of a heat-resistant synthetic resin and rotatably supporting thereon a rotary shaft with air turbine blades fixed thereon, a lubricating oil applied to the rolling bearing element is composed of a nondrying oil out of vegetable oils excellent in biosafety and environmental conservation and superb in heat resistance (so that sterilization and disinfection by autoclaving is feasible) and durability in place of a conventional lubricating oil of the mineral oil base or of the synthetic oil base.

Roughly dividing, vegetable oils can be classified into the following three types:

(i) Nondrying oils:

The term "nondrying oil" means an oil which does not form any film-like matter (resinous solid) even when dried (oxidized) in the form of a thin layer in air.

A nondrying oil of this type contains unsaturated fatty acids, each of which contains two or more double bonds per molecule (hereinafter called "poly-unsaturated fatty acids"), only in small amounts and is primarily composed of the glyceride (glycerol ester) of oleic acid (which contains one double bond per molecule), and its iodine value (a scale indicating the degree of unsaturation of an oil) is 100 or smaller.

Representative examples of nondrying oils of this type can include olive oil, arachis oil and oleysol oil.

(ii) Semidrying oils:

The term "semidrying oil" means an oil which shows intermediate properties between a nondrying oil and a drying oil to be described next. Its iodine value is from 100 to 130.

Representative examples of semidrying oils of this type can include rapeseed oil, sesame oil and cotton seed oil.

(iii) Drying oils:

The term "drying oil" means an oil which forms a film (resinous solid) when dried (oxidized) in the form of a thin layer in air. A drying oil of this type is composed of glycerides of fatty acids having high degrees of unsaturation (for example, linoleic acid contains two double bonds and linolenic contains three double bonds). These glycerides absorb oxygen in air and undergo oxidative polymerization, whereby a film-like matter is easily formed. Incidentally, the iodine value of such a drying oil is 130 or greater.

Typical examples of drying oils of this type can include linseed oil and tung oil.

Among the above-described various vegetable oils, nondrying oils are oils and fats (glycerol esters of fatty acids) each of which does not form a film-like matter (resinous solid) even when dried (oxidized) in the form of a thin layer. As they are excellent in heat resistance (so that sterilization and disinfection by autoclaving is feasible) and durability, they are suitable as lubricating oils for rolling bearings in high-speed rotating equipments such as dental air turbine hand pieces.

As a lubricating oil for a rolling bearing in a high-speed rotating equipment such as a dental air turbine hand piece, the present invention adopts a nondrying oil out of vegetable oils. A description will hereinafter be made in detail about olive oil, a representative example of the above-described nondrying vegetable oils.

Olive oil is an oil (glycerol esters) available from drupes of Olea Europaea. Roughly driving, its components can be classified into the following three types:

(i) unsaturated resin acids;

(ii) saturated resin acids; and (iii) various trace components.

The unsaturated resin acids in olive oil are generally composed of mono-unsaturated and di- and higher-unsaturated (poly-unsaturated) resin acids.

The kinds and contents of the unsaturated resin acids in olive oil will be shown below:

1) Oleic acid (mono-unsaturated) . . . 56.0–83.0%

2) Linoleic acid (poly-unsaturated) . . . 3.5–20.0%

3) Palmitoleic acid (mono-unsaturated) . . . 0.3–3.5%

$$CH_3(CH_2)_5CH=CH(CH_2)_7COOH$$

4) Linolenic acid (poly-unsaturated) . . . 0.0–1.5%

$$CH_3CH_2CH=CHCH_2CH=CHCH_2CH=CH(CH_2)_7COOH$$

5) Gadoleic acid (mono-unsaturated) . . . 0.0–0.05%

$$CH_3(CH_2)_9CH=CH(CH_2)_7COOH$$

As has been described above, olive oil abundantly contains oleic acid which is a mono-unsaturated fatty acid. Olive oil also contains poly-unsaturated fatty acids, such as linoleic acid, in small amounts.

As has also been described above, a poly-unsaturated fatty acid is susceptible to oxidation. Nonetheless, olive oil has excellent oxidation resistance as a whole because, as will be described subsequently herein, olive oil contains tocopherols (vitamin E) as trace components and poly-unsaturated fatty acids such as linolenic acid are protected from oxidative deterioration owing to the anti-oxidation action of the tocopherols (vitamin E).

A description will next be made about saturated fatty acid components in olive oil.

The kinds and contents of saturated fatty acids in olive oil will be shown below:

1) Palmitic acid $CH_3(CH_2)_{14}COOH$ . . . 7.5–20.0%
2) Stearic acid $CH_3(CH_2)_{16}COOH$ . . . 0.5–3.5%
3) Myristic acid $CH_3(CH_2)_{12}COOH$ . . . 0.0–0.05%
4) Arachidic acid $CH_3(CH_2)_{18}COOH$ . . . 0.0–0.05%
5) Behenic acid $CH_3(CH_2)_{20}COOH$ . . . 0.0–0.05%
6) Lignoceric acid $CH_3(CH_2)_{22}COOH$ . . . 0.0–0.05%

As is appreciated from the foregoing, olive oil can be considered to have low contents of saturated fatty acids which cause hypercholesterolemia.

Next, a description will be made of various trace components in olive oil.

The kinds of various trace components in olive oil will hereinafter be described along with their properties and functions.

(1) Unsaponifiable materials:
  (a) Sterols
  (b) Hydrocarbons
    Squalene
    Aromatic hydrocarbons (which impart inherent sensory characteristics, namely, aroma and flavor)
  (c) Tocopherols (oxidation-preventing function)
    α-tocopherol (vitamin E) (prevention of blackening and polymerization)
    β,γ,δ-tocopherols (prevention of rancidity which would otherwise be caused by the existence of one or more heavy metals)
  (d) Triterpene alcohols
    Cycloalterenol
    Erythrodiol
  (e) Fat-soluble vitamins
    Vitamins A, D (anti-oxidation effects)
(2) Phospholipids, chlorophyll and derivatives:
  (a) Phospholipids
  (b) Chlorophyll (anti-oxidation effect)
(3) Phenolic compounds:
  (a) Phenolic compounds (anti-oxidation effects)
  (b) Polyphenols (anti-oxidation effects)

As is appreciated from the foregoing, olive oil has higher contents of various trace components, which act against oxidation of oils and fats, than other nondrying oils and drying oils, and can therefore provide a lubricating oil excellent in heat resistance (so that sterilization and disinfection by autoclaving is feasible) and durability.

A description will next be made about other nondrying vegetable oils which can also make up the lubricating oil according to the present invention for a bearing in a high-speed rotating equipment such as a dental air turbine hand piece.

(i) As a nondrying oil other than the above-described olive oil, there is arachis oil.

Arachis oil is found at a content of 40–50% in seeds of *Arachis hypogaea*, and is derived from its seeds by pressing.

(ii) As a nondrying oil other than the above-described olive oil, there is oleysol oil.

Oleysol oil is available from a mutant species of sunflower, which has a high content of linoleic acid (poly-unsaturated) which is not a nondrying oil. Owing to the efforts of agricultural chemical engineers to date, it has been succeeded in growing a sunflower of mutant species which abundantly contains oleic acid (mono-unsaturated fatty acid). From this mutant species, oil named "Oleysol" is produced. Oleysol oil is a nondrying oil similar to the above-described olive oil.

Differences between certain nondrying vegetable oils, which can make up lubricating oils for rolling bearings according to the present invention for high-speed rotating equipments such as dental air turbine hand pieces, and some semidrying vegetable oils and other edible oils are shown below in Table 1. In Table 1, olive oil, arachis oil and oleysol oil are nondrying vegetable oils useful for rolling bearings according to the present invention, while the remaining oils indicate semidrying vegetable oils and drying oils as controls.

In Table 1, the notes have the following meanings:
(1) composed primarily of oleic acid, and containing palmitoleic acid,
(2) linoleic acid,
(3) linolenic acid, and
(4) composed of palmitic acid, stearic acid, lauric acid and myristic acid.

In Table 1, asterisk (*) indicates control vegetable oils.

TABLE 1

Comparison between Nondrying Vegetable Oils and Other Edible Oils

| | Average constituent fatty acids (%) | | | | | Ratio of vitamin E/ poly-unsaturated fatty acids (mg/g) |
|---|---|---|---|---|---|---|
| | Unsaturated fatty acids | | | Saturated fatty acids | Vitamin E (mg/kg) | |
| | Mono- (1) | Di- (2) | Tri- (3) | (4) | | |
| Olive oil | 70 | 12 | 0.5–1.5 | 15 | 150 | 1.11 |
| Arachis oil | 60 | 25 | — | 15 | 150 | 0.60 |
| Oleysol oil | 80 | 10 | | 10 | | |
| rapeseed oil* | 60 | 22 | 10 | 8 | 150 | 0.47 |
| Sunflower oil* | 20 | 70 | 10 | 10 | 250 | 0.315 |
| Soybean oil* | 23 | 55 | 7 | 15 | 175 | 0.28 |
| Corn oil* | 26 | 60 | 2 | 12 | 200 | 0.32 |
| Coconut oil* (solid fat) | 8 | 2 | <1 | 90 | | |

From Table 1, the following tendencies are apparent.
(i) A nondrying vegetable oil contains oxidation-resistant mono-unsaturated fatty acids in a large total amount.
(ii) A nondrying vegetable oil contains oxidation-susceptible di- to tri-unsaturated fatty acids, namely, poly-unsaturated fatty acids in a small total amount.

(iii) A nondrying vegetable oil contains tocopherols (vitamin E and the like) having anti-oxidation effects at a high ratio relative to poly-unsaturated fatty acids.

In nondrying vegetable oils (olive oil, arachis oil, oleysol oil, and the like) which can make up lubricating oils for rolling bearings according to the present invention in high-speed rotating equipments such as dental air turbine hand pieces, lubrication characteristics become better as the total content of free fatty acids (saturated and unsaturated) becomes lower.

These tendencies were found in the course of the present inventors' investigation toward improvements in the lubricating characteristics of nondrying vegetable oils and, as will be explained subsequently herein, are supported by substantiating data.

Concerning the above-mentioned fatty acids (which may hereinafter be called "free fatty acids") liberated into a nondrying vegetable oil, a description will hereinafter be made.

In general, an oil or fat (a fat such as beef tallow, lard or butter; or a fatty oil such as rapeseed oil, tung oil or linseed oil) is composed of glycerol esters of higher fatty acids.

Namely, in a nondrying vegetable oil useful for a rolling bearing according to the present invention, various fatty acids (saturated and unsaturated) exist as esters represented by the following formula (1):

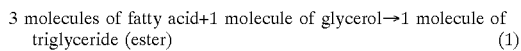

3 molecules of fatty acid+1 molecule of glycerol→1 molecule of triglyceride (ester)     (1)

However, the nondrying vegetable oil also contains various fatty acids (free fatty acids) which are not combined with glycerol ($CH_2OH$—$CHOH$—$CH_2OH$). Expressing the total content of the above-mentioned free fatty acids in terms of free acid value, the lower this value, the lower the acidity and the more shifted toward a higher viscosity side the viscosity. A nondrying vegetable oil having a lower free acid value is therefore excellent in durability as a lubricating oil for a rolling bearing.

Based on the above-described free acid value, olive oil is classified in quality as shown below in Table 2. As will be apparent from Table 2, olive oil of higher quality has a lower free acid value and, as will be described subsequently herein, shows better lubricating characteristics (see Table 3).

To lower the free acid value of a nondrying vegetable oil such as olive oil, a method to be described next can be adopted by way of example. Namely, when olive oil is heated subsequent to addition of a 5–10% aqueous solution of sodium hydroxide, the olive oil is saponified to form glycerol and the sodium salts of fatty acids. The resulting glycerol esterifies free fatty acids. Subsequent removal of oils and fats by centrifugation can provide olive oil having a low free acid value.

In Table 2, the names of various grades of olive oil are trade names of olive oils produced by Golden Eagle Olive Products, U.S.A.

TABLE 2

Free Acid Values of Olive Oil

| Grade of olive oil | Free acid value (wt. %) |
|---|---|
| Refined oil | 0.1 |
| Extra virgin oil | 1.1 |
| Virgin oil | 3.2 |

The present invention will hereinafter be described in further detail by the following example.

In particular, lubrication systems according to the present invention, each of which comprised a retainer composed of a molded porous resin body and a lubricating oil composed primarily of a nondrying vegetable oil, were compared with lubrication systems making use of conventionally known lubricating oils in a rolling bearing of a dental air turbine hand piece to substantiate the superiority of the lubrication systems of the present invention.

(i) Overall constructions of the retainers:

A rolling bearing of a dental air hand piece (see FIG. 1 to FIG. 2) furnished for use in a test of this example had the following construction:

Miniature rolling bearing of the open type, which was provided with a snap retainer and had the following dimensions:
(i) Inner diameter of an outer ring: 6.350 mm
(ii) Inner diameter of an inner ring: 3.175 mm
(iii) Width: 2.380 mm The above bearing was assembled in the dental air turbine hand piece, and the test was conducted under the following conditions: air supply pressure, 2.5 kg/cm$^2$; air supply rate, 26 l/min; revolution speed, about 400,000 rpm.

(ii) Kinds of retainers:

(1) Non-porous PI/PAI.R:

This means a non-porous retainer of the polyimide (PI) base or the polyamideimide (PAI) base.

The non-porous PI.R was obtained by forming "Vespel SP-1" (trade name, product of E. I. du Pont de Nemours & Co., Ltd.) into a retainer-like shape.

On the other hand, the non-porous PAI.R was obtained by forming "Torlon 4203" (trade name, product of Teijin-Amoco Engineering Plastics, Ltd.) into a retainer-like shape.

(2) Porous P.R:

This means a porous retainer made of a fabric-containing phenol resin.

The porous P.R was obtained by impregnating inter-thread spaces of a woven fabric, which had been rolled plural times into a pipe-like shape, with a phenol resin in a vacuum state, shaping the thus-impregnated fabric under heat and then machining the shaped fabric into a retainer-like shape.

(3) Porous PI/PAI.R:

This means a porous retainer of the polyimide (PI) base or polyamideimide (PAI) base. The porous PI.R was obtained by compression-molding "UIP-S" (trade name, product of Ube Industries, Ltd.) under a molding pressure of 4000 kgf/cm$^2$, sintering the green compact at 400° C. in a nitrogen gas atmosphere and then machining the sintered compact into a retainer-like shape (porosity: about 13% by volume).

The porous PAI.R was obtained by classifying and sifting "Torlon 4000TF" (trade name, product of Amoco Chemical Corp., U.S.A.) into an average particle size of 20 μm, compression-molding the thus-shifted powder under a preforming pressure of 2,800 kgf/cm$^2$, sintering the green compact at 300° C., and then machining the sintered compact into a retainer-like shape (porosity: about 14% by volume).

The test results of the lubrication systems according to the present invention, each of which comprised the retainer composed of the molded porous resin body and the lubricating oil composed primarily of the nondrying vegetable oil, and the lubrication systems making use of the conventionally known lubricating oils as tested in the rolling bearing of the dental air turbine hand piece (see FIG. 1 to FIG. 2) are shown below in Table 3.

In Table 3, the notes have the following meanings:
(1) <Heat resistance test (autoclaving resistance; cycles)>

An autoclaving apparatus ("ALPHI", trade name; manufactured by J. MORITA MFG. CORP.) was used. Autoclaving resistance is expressed in terms of cycles until the rotation of the dental air turbine hand piece became unstable and the efficiency of rotation dropped to 10% (about 40,000 rpm).

Conditions for the treatment in the autoclaving apparatus "ALPHI" were: steam pressure, 2.4 kg/cm$^2$; temperature, 135° C.; time, 5 minutes.

(2) <Bearing resistance (continuous operation; hrs)>

Each lubricating oil was applied to a lubrication system of the dental air hand piece at the beginning, and a continuous operation was then performed at about 400,000 rpm without additional feeding of the lubricating oil. The bearing resistance is expressed in term of hours until the rotation become unstable and the revolution speed dropped to 10% (about 40,000 rpm).

In Table 3,
(a) As the paraffin oil (liquid paraffin), a conventional spray-type paraffin oil produced by an odontotherapy-related maker was used.
(b) As the fluorinated oil, "FOMBLIN" (trade name, product of Ausimont S.p.A., Italy) was used.

TABLE 3

Evaluation of Characteristics of Various Lubricating Oils

| Lubricating oil | | | Bio-safety | Environmental Conservation | Heat resistance (1) (autoclaving resistance, cycles) | | | Bearing resistance (2) (continuous rotation, hrs) | | |
|---|---|---|---|---|---|---|---|---|---|---|
| | | | | | (i) Non-porous PI/PAI·R | (ii) Porous P·R | (iii) Porous PI/PAI·R | (i) Non-porous PI/PAI·R | (ii) Porous P·R | (iii) Porous PI/PAI·R |
| Vegetable oil | Nondrying oil | Refined olive oil | A | B | 1000< | 1000< | 1000< | 1.50 | 25.00 | 29.75 |
| | | Extra virgin olive oil | A | B | 1000< | 1000< | 1000< | 2.00 | 23.50 | 25.50 |
| | | Virgin olive oil | A | B | 1000< | 1000< | 1000< | 1.75 | 16.50 | 18.25 |
| | | Arachis oil | A | B | 1000< | 1000< | 1000< | 1.50 | 14.75 | 18.50 |
| | Semidrying oil | Rapeseed oil | A | B | 300 | 300 | 300 | 0.25 | 2.25 | 4.50 |
| Mineral oil | Paraffin oil | | C | C | 1000< | 200 | 1000< | 0.50 | 6.75 | 8.50 |
| Synthetic oil | Fluorinated oil | | C | C | 1000< | 1000< | 1000< | 1.50 | 14.50 | 17.50 |

A: Excellent, B: Good, C: Poor

As is shown in Table 3, it is appreciated that the lubricating oils suitable for the bearing according to the present invention, said lubricating oils being composed primarily of the nondrying vegetable oils respectively, are excellent in the various characteristics of biosafety, environmental conservation, heat resistance (autoclaving resistance) and bearing durability compared with the conventional lubricating oils.

We claim:

1. A rolling bearing for a high-speed rotating equipment, said rolling bearing being constructed of an outer ring, an inner ring, rolling elements and a retainer to rotatably support at least a rotary shaft thereon, wherein:
   (i) said retainer is composed of a molded porous synthetic resin body having a porous portion of a communicated structure in at least a part thereof; and
   (ii) said retainer is lubricated with a lubricating oil comprising a nondrying vegetable oil.

2. The bearing according to claim 1, wherein said molded porous synthetic resin body having said porous portion of said communicated structure is selected from:
   (1) a molded polyimide resin body having a porous portion of a communicated structure a porosity of which is from 5 to 20% by volume, or
   (2) a shaped phenol resin body having, as a porous portion of a communicated structure, a fiber layer a porosity of which is from 5 to 20% by volume.

3. The bearing according to claim 2, wherein said molded polyimide resin body having said porous portion of said communicated structure has been fabricated by sintering a resin powder compact.

4. The bearing according to claim 2, wherein said shaped phenol resin body having said porous portion of said communicated structure has a fiber layer, and said fiber layer makes up said porous portion of said communicated structure.

5. The bearing according to claim 1, wherein said nondrying vegetable oil comprises:
   (i) at least 60 wt. % of at least one mono-unsaturated fatty acid, said mono-unsaturated fatty acid containing one unsaturated bond per molecule; and
   (ii) at most 30 wt. % of at least one poly-unsaturated fatty acid, said poly-unsaturated fatty acid containing at least two unsaturated bonds per molecule.

6. The bearing according to claim 5, wherein said nondrying vegetable oil comprises at most 10 wt. % of a tocopherol.

7. The bearing according to claim 5, wherein said nondrying vegetable oil is selected from a group consisting of olive oil, arachis oil and oleysol oil.

8. The bearing according to claim 7, wherein said nondrying vegetable oil comprises at most 5 wt. % of saturated and unsaturated fatty acids not combined with glycerin (free fatty acids).

* * * * *